United States Patent
Qin et al.

(10) Patent No.: US 11,926,869 B2
(45) Date of Patent: Mar. 12, 2024

(54) DEVELOPMENT OF SIMPLE SEQUENCE REPEAT (SSR) CORE PRIMER GROUP BASED ON WHOLE GENOME SEQUENCE OF POMEGRANATE AND APPLICATION THEREOF

(71) Applicant: Institute of Horticulture Research, Anhui Academy of Agricultural Science, Hefei (CN)

(72) Inventors: Gaihua Qin, Hefei (CN); Yiliu Xu, Hefei (CN); Chunyan Liu, Hefei (CN); Jiyu Li, Hefei (CN)

(73) Assignee: INSTITUTE OF HORTICULTURE RESEARCH, ANHUI ACADEMY OF AGRICULTURAL SCIENCE, Hefei (CN)

( * ) Notice: Subject to any disclaimer, the term of this patent is extended or adjusted under 35 U.S.C. 154(b) by 0 days.

(21) Appl. No.: 17/877,908

(22) Filed: Jul. 30, 2022

(65) Prior Publication Data
US 2023/0069872 A1 Mar. 9, 2023

Related U.S. Application Data

(63) Continuation of application No. 16/926,735, filed on Jul. 12, 2020, now abandoned.

(30) Foreign Application Priority Data

Jul. 12, 2019 (CN) .......................... 201910631857.6

(51) Int. Cl.
*C12Q 1/6858* (2018.01)
*C12Q 1/6895* (2018.01)

(52) U.S. Cl.
CPC ......... *C12Q 1/6858* (2013.01); *C12Q 1/6895* (2013.01); *C12Q 2531/113* (2013.01); *C12Q 2565/125* (2013.01); *C12Q 2600/156* (2013.01)

(58) Field of Classification Search
None
See application file for complete search history.

(56) References Cited

PUBLICATIONS

Hasnaoui et al., "Development and characterization of SSR markers for pomegranate (*Punica granatum* L.) using an enriched library," Conservation Genet. Resour., vol. 2, pp. 283-285. (Year: 2010).*

* cited by examiner

*Primary Examiner* — Young J Kim
(74) *Attorney, Agent, or Firm* — ScienBiziP, P.C.

(57) ABSTRACT

The development of a simple sequence repeat (SSR) core primer group based on the whole genome sequence of pomegranate and the applications thereof are disclosed. The primer group includes 11 primer pairs: PG080, PG130, PG139, PG152, PG153, PG140, PG098, PG070, PG077, PG090, and PG093. The SSR core primer group of the present disclosure has the advantages such as high polymorphism, good repeatability, stable amplification, and clear and easy to score bands, and is applicable to the fields of pomegranate variety identification, DNA fingerprinting construction, genetic diversity assessment and phylogenetic study, and the like, providing a new tool for pomegranate molecular marker-assisted selection and having an excellent application prospect.

3 Claims, 2 Drawing Sheets

Specification includes a Sequence Listing.

DEVELOPMENT OF SIMPLE SEQUENCE REPEAT (SSR) CORE PRIMER GROUP BASED ON WHOLE GENOME SEQUENCE OF POMEGRANATE AND APPLICATION THEREOF

RELATED APPLICATIONS

This Continuing Application claims priority to the Non-provisional application Ser. No. 16/926,735 filed on Jul. 12, 2020, which claims priority under 35 U.S.C. § 119(a) on Patent Application No. 201910631857.6 filed in China on Jul. 12, 2019, the entire contents of which are hereby incorporated by reference.

SEQUENCE LISTING

The Sequence Listing associated with the present application is provided in XML format, and is hereby incorporated by reference in its entirety into the specification. The name of the XML file containing the Sequence Listing is entitled "US87987-SeqListing_ST26XML". The XML file was created on Oct. 3, 2022, having a size of about 29,000 bytes, and is being submitted electronically via EFS-Web.

FIELD

The present disclosure relates to a field of molecular biotechnology, in particular to development of a simple sequence repeat (SSR) core primer group using whole genome sequence of pomegranate and applications in pomegranate variety identification, DNA fingerprinting construction, and genetic diversity assessment and phylogenetic study.

BACKGROUND

Microsatellite (Simple Sequence Repeat, SSR) markers are short tandemly repeated motifs of 1~6 nucleotides that abundantly present throughout the genome. SSRs have the characteristics of wide distribution, codominant inheritance, high polymorphism, convenient detection, and good stability, and are widely used in many research fields such as variety identification, genetic diversity assessment and phylogenetic relationship study, and genetic map construction and quantitative trait locus (QTL) mapping. At the early stage of SSR development, the study of SSR markers was mainly based on genomic DNA libraries or specific microsatellite-enriched libraries. Such development methods create heavy workloads, while only a very limited number of SSR markers could be obtained. In recent years, the development of SSR markers based on the whole genome sequence is able to acquire abundant markers, which could cover the entire genome and evenly distribute across the genome, so it is widely used in a variety of sequenced plants.

Pomegranate was one of the edible fruit trees recognized by humans previously, native to the Persian region (present-day Iran), and domesticated by humans in the fifth century BC. Now, pomegranate is widely cultivated in countries with Mediterranean-like climates around the world, including Tunisia, Turkey, Spain, Egypt, Morocco, the USA, China, India, Argentina, Israel, and South Africa. It is widely consumed in the form of fruits, juice, wines, and medicines due to its nutritional, medicinal, and ornamental values. According to the records, pomegranate was introduced to China when Qian Zhang served as an imperial envoy to the Western Regions, Xiyu, during the Han Dynasty, and has been cultivated in China for more than 2000 years. Pomegranate is diversified, as recorded in the "China Fruit Tree Record, Volume of Pomegranate", there are more than 300 pomegranate genetic resources in China. Pomegranate can be divided into sweet pomegranate and sour pomegranate according to the flavor, hard-seeded pomegranate and soft-seeded pomegranate according to the hardness of seed, ornamental pomegranate and edible pomegranate according to the utilization, red skin, white skin, yellow skin, and pink skin pomegranate according to the color of pericarp, etc. Genetic exchange and variety introduction happen frequently in different local areas, and they are carried out usually basing on the local production and fruit characterization, so homonym and synonym are existed generally. The cultivation range of pomegranate is expanded gradually, which results in serious mixing between pomegranate varieties, bringing new challenges to pomegranate producers and breeders.

Based on long history of pomegranate cultivation, abundant pomegranate resources, and frequent exchanges of varieties, it is important and of practical significance to develop pomegranate variety identification, DNA fingerprinting construction, genetic diversity assessment and phylogenetic relationship study. The insensitivity of SSR markers to environmental changes and desirable genetic attributes make them valuable for variety identification and evaluating germplasm diversity. However, the SSRs of pomegranate were mainly developed from enriched genomic libraries, which is a time-consuming and laborious process. Identification of SSRs from the genome sequence has been proved to be a robust, rapid, and widely strategy. Thus, it is of great value to develop SSR marker core primers on the whole genome according to the existing genome sequence of pomegranate.

BRIEF DESCRIPTION OF THE DRAWINGS

Aspects of the present disclosure are best understood from the following detailed disclosure when read with the accompanying drawings. Various features are not drawn to scale. Dimensions of various features may be arbitrarily increased or reduced for clarity of discussion.

DESCRIPTION

The present disclosure is to provide rapid development of simple sequence repeat (SSR) markers using whole genome data to screen primer groups, these primers have the advantages of stable amplification, clear bands, and high polymorphism, and can be effectively applied to the fields of pomegranate variety identification, DNA fingerprinting construction, genetic diversity assessment and phylogenetic study, and the like.

According to a first aspect of the present disclosure, a developed SSR core primer group based on the whole genome sequence of pomegranate is provided. The primer group comprises 11 primer pairs including PG080, PG130, PG139, PG152, PG153, PG140, PG098, PG070, PG077, PG090, and PG093, the nucleotide sequence of each primer is sequentially shown as in Table 2 below. Each of the 11 primer pairs includes a forward primer and a corresponding reverse primer.

According to a second aspect of the present disclosure, a method for development of the SSR core primer group based on the whole genome sequence of pomegranate is provided, the method includes:

(1) pomegranate genomic deoxyribonucleic acid (DNA) extraction: a hexadecyltrimethylammonium bromide (CTAB) method is utilized to extract DNA, the extracted DNA is added with 50 μL of 0.1 M Tris-EDTA (TE) buffer for dissolving overnight and then stored at −20° C. until use;

(2) whole genome data of pomegranate is downloaded from DDBJ/ENA/GenBank databases under an accession number MTKT00000000; MISA software (MIcroSAtellite identification tool) is used to mine SSR loci with different repeat units within the range of the whole genome, the SSR search criteria are 11 repeat units for dinucleotide repeats, 8 repeat units for trinucleotide repeats, 6 repeat units for tetranucleotide repeats, 5 repeat units for pentanucleotide repeats, and 4 repeat units for hexanucleotide repeats;

(3) SSR primer design from the obtained SSR loci above, 5 SSR loci are randomly selected on each chromosome, the primers are designed by Primer 3.0 using the flanking sequences of SSRs, the parameters for the primer design are as follows: a length of the PCR products is in a range of 100~350 bp; a melting temperature (Tm) is between 50~70° C., ensuing a difference in Tm value between two primers does not exceed 4° C.; a GC % content is between 40~65%; a length of the primers is in a range of 18~28 bp; in order to ensure the specificity of the primers, the conserved flanking sequences and the SSR lociused for the primer design are at least 20~23 bases apart; 45 primer pairs are successfully designed using the above-described method; and (4) primer screening genomic DNA of 6 representative pomegranate accessions from different production areas of China is amplified using the newly designed 45 primer pairs, PCR amplification is conducted in 20 μL of reaction mixture containing 1.0 ng of DNA, 0.4 μM of forward primers, 0.4 μM of reverse primers, 4 mM of $MgCl_2$, 400 μM of dNTPs, 1.0 U of Taq-DNA polymerase, and $ddH_2O$ to the total volume of 20 μL. Touchdown PCR is carried out under the following conditions: 5 min at 95° C., followed by 11 cycles with a decrease of 0.8° C. in the melting temperature after each cycle {30 s at 95° C.; 30 s at 65° C.; 50 s at 72° C.}, followed by 22 cycles {30 s at 95° C.; 30 s at 55° C.; 50 s at 72° C.}, and a final extension of 8 min at 72° C.; fragment sizes of the PCR products are determined by capillary electrophoresis, 11 primer pairs with stable amplification, clear bands, and high polymorphism are selected according to the results from the amplification.

According to a third aspect of the present disclosure, an application of the developed SSR core primer group based on the whole genome sequence of pomegranate in pomegranate variety identification is provided.

The above-mentioned variety identification is to use 11 primer pairs that are carried out a capillary electrophoresis with fluorescence detection. According to the results of the capillary electrophoresis detection, variety identification is determined by the number of differential loci, two varieties having differential loci ≥3 are considered as different varieties, those having differential loci <3 are considered as substantially similar or the same variety.

According to a fourth aspect of the present disclosure, an application of the developed SSR core primer group in pomegranate DNA fingerprinting construction is provided.

According to a fifth aspect of the present disclosure, genetic diversity assessment and phylogenetic research on pomegranate genetic diversity assessment and phylogenetic research applications are provided.

The beneficial effects and/or advantages of the present disclosure include:

1. The present disclosure newly develops a group of pomegranate SSR core primers, which enriched pomegranate SSR marker library.
2. The present disclosure establishes a method for developing an SSR core primer group in the pomegranate whole-genome scale. While comparing to other methods, the method of the present disclosure has the characteristics such as easy development, low cost, and high efficiency, and is able to acquire abundant markers in genome wide, which randomly distributes in 9 chromosomes, and has important practical values.
3. The 11 SSR core primer pairs developed from the present disclosure have the advantages such as high polymorphism, good repeatability, stable amplification, and clear and easy to score bands, and are applicable to the fields of pomegranate variety identification, DNA fingerprinting construction, genetic diversity assessment and phylogenetic study, and the like, providing a new tool for pomegranate molecular assisted breeding and having an excellent application prospect.

Figure 1:
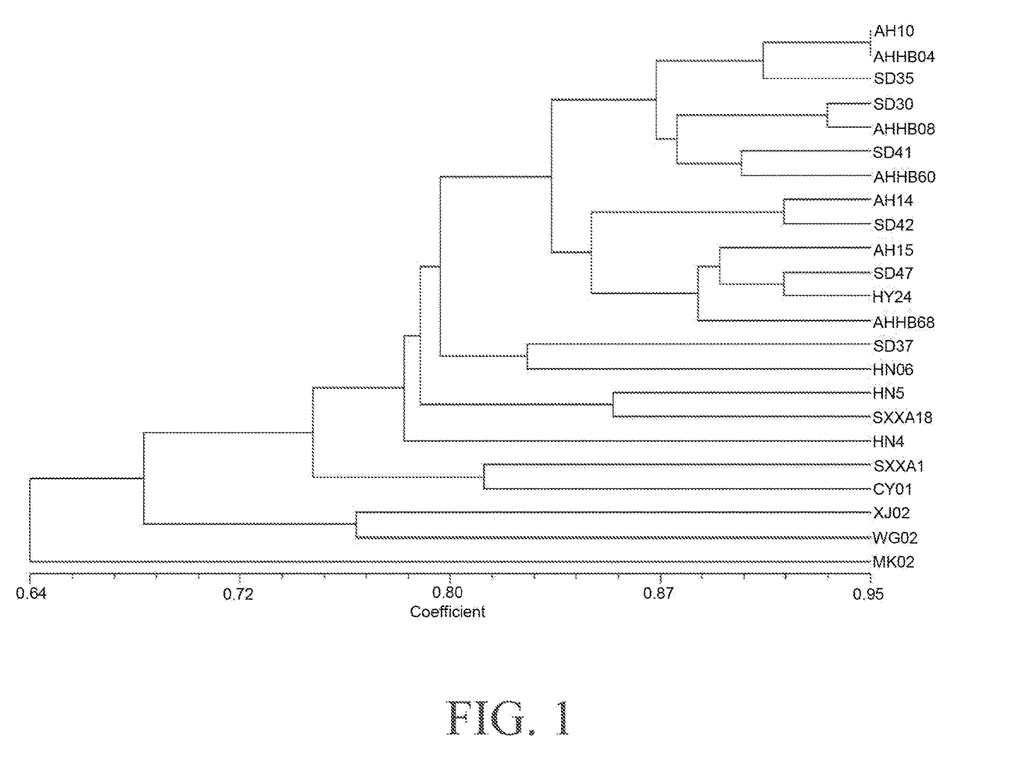
FIG. 1 is a diagram illustrating a phylogenetic tree, according to an example implementation of the present disclosure.

The drawing is a phylogenetic tree of 23 pomegranate accessions.

The present disclosure is further explained in combination with the implementations and drawings. The following implementations are used in the present disclosure for illustration purposes only, and are not intended to limit the scope of the present disclosure.

I. Pomegranate Genomic DNA Extraction (1) Selection of 23 pomegranate accessions from different production areas.

Names and origins of the 23 pomegranate accessions are shown in Table 1.

TABLE 1

Information of 23 pomegranate accessions

| Accession | Origin |
| --- | --- |
| AH10 | Anhui, China |
| AH14 | Anhui, China |
| AH15 | Anhui, China |
| AHHB04 | Anhui, China |
| AHHB08 | Anhui, China |
| AHHB60 | Anhui, China |
| AHHB68 | Anhui, China |
| SD35 | Shandong, China |
| SD30 | Shandong, China |
| SD41 | Shandong, China |
| SD42 | Shandong, China |
| SD47 | Shandong, China |
| SD37 | Shandong, China |
| HN5 | Henan, China |
| HN06 | Henan, China |
| HN4 | Henan, China |
| SXXA18 | Shanxi, China |
| SXXA1 | Shanxi, China |

TABLE 1-continued

Information of 23 pomegranate accessions

| Accession | Origin |
| --- | --- |
| CY01 | Xizang, Tibet Autonomous Region |
| XJ02 | Xinjiang Uygur Autonomous Region |
| WG02 | USA |
| MK02 | Xizang, Tibet Autonomous Region |
| HY24 | Anhui, China |

(2) Genomic DNA extraction using CTAB method.

0.2~0.3 g of fresh leaves are weighed and added with liquid nitrogen to quickly grind into a fine powder. The powder is transferred into a 2.0 mL centrifuge tube, mixed with 1.0 mL of pre-heated (65° C.) 3×CTAB extraction buffer, and incubated into a 65° C. water bath for 1 h. After incubation, the sample is centrifuged at a speed of 12000 rpm for 10 min at room temperature, and the supernatant is transferred into a clean 2.0 mL centrifuge tube. The supernatant is added with an equal volume of phenol/chloroform/isoamyl alcohol (25:24:1, V/V/V) and gently mixed by inversion to form an emulsion. The emulsion is centrifuged at the speed of 12000 r/min for 8 min, and the supernatant is collected and added with an equal volume of chloroform/isoamyl alcohol (24:1, V/V), after gently mixing, the sample is centrifuged at the speed of 12000 r/min for 8 min. The supernatant is collected, added with an equal volume of ice-cold isopropyl alcohol and 10 µL of 3M sodium acetate, and placed for 30 min at −20° C. to precipitate. The sample is then centrifuged at the speed of 12000 r/min for 8 min, the supernatant is carefully decanted away while DNA is remained in the centrifuge tube. The DNA is washed with 75% ethanol twice and absolute ethanol once, centrifuged to remove the absolute ethanol, and allowed to dry at room temperature. The DNA is then added with 50 µL of TE buffer (0.1 M) to dissolve overnight and stored at −20° C. until use.

II. Development of SSR Primers of Pomegranate Genome (1) Whole genome data of pomegranate is downloaded from DDBJ/ENA/GenBank databases under an accession number MTKT00000000. ERISA software (MIcroSAtellite identification tool, pgrc.ipk-gatersleben.de/misa) is used to mine SSR loci with different repeat units within the range of the whole genome. The SSR search criteria are 11 repeat units for dinucleotide repeats, 8 repeat units for trinucleotide repeats, 6 repeat units for tetranucleotide repeats, 5 repeat units for pentanucleotide repeats, and 4 repeat units for hexanucleotide repeats.

(2) SSR primer design

From the obtained SSR loci above, 5 SSR loci are randomly selected on each chromosome, the primers are designed by Primer 3.0 using the flanking sequences of SSRs. The parameters for the primer design are as follows: a length of the PCR products is in a range of 100~350bp; a melting temperature (Tm) is between 50~70° C., ensuing a difference in Tm value between two primers does not exceed 4° C.; a GC % content is between 40~65%; a length of the primers is in a range of 18~28 bp; and the primers are best to have a 5' end of G/C and avoid a 3' end of A. In order to ensure the specificity of the primers, the conserved flanking sequences and the SSR lociused for the primer design are at least 20~23 bases apart. 45 primer pairs are successfully designed using the above-described method, and the primers are synthesized by Sangon Biotech Company (Shanghai, China).

(3) Primer screening

Genomic DNA of 6 representative pomegranate accessions (AHHB04, SXXA1, CY01, XJ02, HN4, and SD47, which were originated from Anhui province, Shanxi province, Tibet Autonomous Region, Xinjiang Uygur Autonomous Region, Henan province, and Shandong province in China, respectively) is amplified using the newly designed 45 primer pairs, 11 primer pairs (Table 2) with stable amplification, clear bands, and high polymorphism are selected according to the results from the amplification.

TABLE 2

Primer sequences of 11 primer pairs

| Sequence ID | Primer | Forward primer | Sequence ID | Primer | Reverse primer |
| --- | --- | --- | --- | --- | --- |
| 1 | PG080 | ctgactgttg cagagagtag gctg | 2 | PG080 | aggaggtgaa acaacgaata gctg |
| 3 | PG130 | ctcatatggc gattctctgt cctt | 4 | PG130 | aagttcgata aattgcactg gtgg |
| 5 | PG139 | gtttccttcc ctcaacccaa aa | 6 | PG139 | agtgggattt taccaagtcg aaca |
| 7 | PG152 | catcagaatc gtccccttgt g | 8 | PG152 | cagagagaag aagagagacc gagc |
| 9 | PG153 | gtgtttgatg ctcccatttc attt | 10 | PG153 | gccttcaacg gtctttcttc ttct |
| 11 | PG140 | caagaaagtg tgtgagcgat tgat | 12 | PG140 | ccaaaccttac ccctctctc tctc |
| 13 | PG098 | tgccttctta aggacttcac caac | 14 | PG098 | ctaacctcat gcacttgtca tcca |
| 15 | PG070 | cacctctgct tcagcaaaca aata | 16 | PG070 | caactcaaca caatatccaa ccca |
| 17 | PG077 | gtcagtctcc tccttcttca atgg | 18 | PG077 | agacgaagca cctgagaagg aat |
| 19 | PG090 | attcttttat actaaccaaa atttgcga | 20 | PG090 | atgtcatgag aggacccaca aa |
| 21 | PG093 | cgtcaatagg acgtccctga gata | 22 | PG093 | gatgacgtgg cagagtaaga gagc |

(4) PCR amplification and capillary electrophoresis of 23 pomegranate accessions using the 11 primer pairs PCR amplification is conducted in 20µL of reaction mixture containing 1.0 ng of DNA, 0.4 µM of forward primers, 0.4 µM of reverse primers, 4mM of $MgCl_2$, 400 µM of dNTPs, 1.0 U of Taq-DNA polymerase, and dd$H_2O$ to the total volume of 20 µL. Touchdown PCR is carried out under the following conditions: 5 min at 95° C.; followed by 11 cycles, with a decrease of 0.8° C. in the melting temperature after each cycle {30 s at 95° C.; 30 s at 65° C.; 50 s at 72°

C.}; followed by 22 cycles {30 s at 95° C.; 30 s at 55° C.; 50 s at 72° C.}; and a final extension of 8 min at 72° C.

Fragment sizes of the PCR products are determined by capillary electrophoresis. The capillary electrophoresis is carried out by the following operations: the PCR products labeled with 6-FAM or HEX fluorescent dye are diluted 30 times using ultrapure water, 1 μL of the diluted PCR products is transferred to a deep well plate dedicated to DNA analyzer. Each well of the well plate is respectively added with 0.1 μL of GeneScan LIZ500 internal size standard and 8.9 μL of deionized formamide to denature for 5 min at 95° C. and then cool for 10 min at 4° C. After short run centrifugation of 10 s, an automatic fluorescence detection is performed by a DNA analyzer (ABI3730XL).

(5) Results and analysis

The DNA fragments are scored on the basis of allele size. The homozygous allelic variation is recorded as X/X, where X represents the size of allelic variation at the locus. The heterozygous allelic variation is recorded as X/Y, where X and Y are two different allelic variations at the locus, small fragments in the front and large fragments in the back. The constructed fingerprinting of 23 pomegranate accessions is shown in Table 3.

Figure 2:
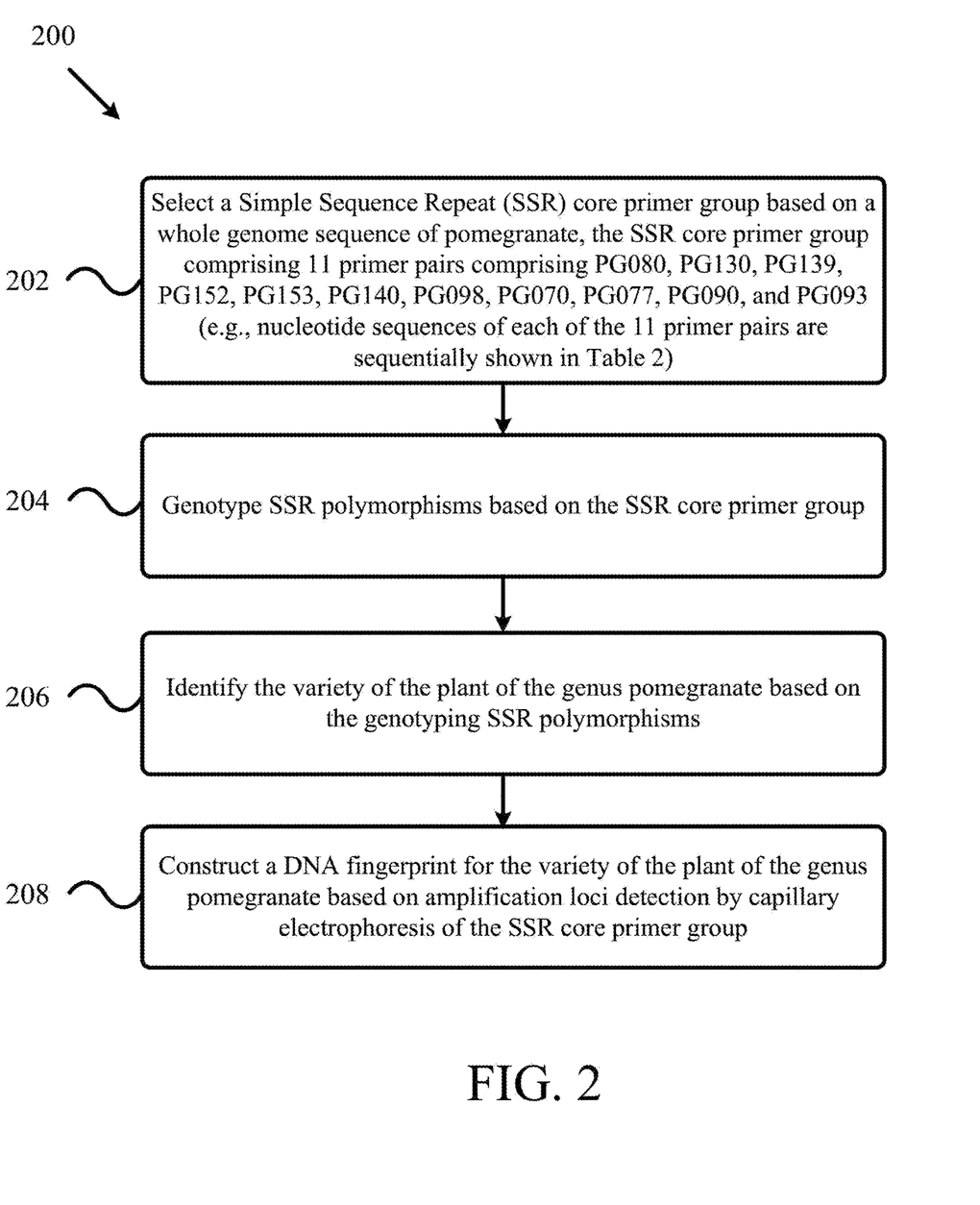
FIG. 2 is a flowchart illustrating a method for identifying a variety of a plant of a genus pomegranate, according to an example implementation of the present disclosure.

FIG. 2 is a flowchart illustrating a method for identifying a variety of a plant of a genus pomegranate, according to an example implementation of the present disclosure. As shown in FIG. 2, flowchart 200 includes actions 202, 204, 206, and 208. Action 202 may include selecting a Simple Sequence Repeat (SSR) core primer group based on a whole genome sequence of pomegranate, the SSR core primer group comprising 11 primer pairs comprising PG080, PG130, PG139, PG152, PG153, PG140, PG098, PG070, PG077, PG090, and PG093. In one implementation, nucleotide sequences of each of the 11 primer pairs are sequentially shown in Table 2 above. Action 204 may include genotyping SSR polymorphisms based on the SSR core primer group. Action 206 may include identifying the variety of the plant of the genus pomegranate based on the genotyping SSR polymorphisms. Action 208 may include constructing a DNA fingerprint for the variety of the plant of the genus pomegranate based on amplification loci detection by capillary electrophoresis of the SSR core primer group.

In view of the present disclosure, it is obvious that various techniques may be used for implementing the disclosed concepts without departing from the scope of those con-

TABLE 3

Fingerprint data of 23 pomegranate accessions

| Sample | PG098 | PG070 | PG130 | PG090 | PG152 | PG153 | PG139 | PG077 | PG093 | PG140 | PG080 |
|---|---|---|---|---|---|---|---|---|---|---|---|
| AH10 | 213/229 | 224/224 | 158/158 | 222/226 | 142/154 | 157/157 | 158/162 | 153/159 | 164/170 | 154/154 | 157/183 |
| AH14 | 213/229 | 224/224 | 158/158 | 222/226 | 154/154 | 157/157 | 162/162 | 153/153 | 164/166 | 154/154 | 157/183 |
| AH15 | 229/229 | 224/224 | 158/158 | 222/222 | 154/154 | 157/157 | 158/162 | 153/161 | 158/166 | 154/156 | 157/157 |
| AHHB04 | 213/213 | 224/224 | 158/158 | 222/222 | 142/154 | 157/157 | 158/162 | 153/159 | 164/170 | 154/154 | 157/157 |
| AHHB08 | 229/229 | 224/224 | 158/158 | 222/226 | 142/142 | 163/163 | 162/162 | 159/159 | 164/170 | 154/154 | 157/183 |
| AHHB60 | 213/229 | 224/224 | 158/158 | 226/226 | 142/142 | 163/163 | 158/158 | 153/153 | 164/164 | 154/154 | 157/183 |
| AHHB68 | 229/229 | 202/224 | 158/158 | 222/226 | 154/154 | 157/157 | 162/162 | 153/161 | 156/170 | 154/154 | 157/157 |
| SD35 | 213/229 | 224/224 | 158/158 | 222/222 | 142/154 | 163/163 | 158/162 | 153/153 | 170/170 | 154/154 | 157/157 |
| SD30 | 229/229 | 224/224 | 158/158 | 222/226 | 142/154 | 163/163 | 158/158 | 157/159 | 164/170 | 154/154 | 157/183 |
| SD41 | 229/229 | 224/224 | 158/158 | 222/226 | 142/142 | 157/163 | 158/162 | 153/153 | 164/166 | 154/154 | 183/183 |
| SD42 | 213/229 | 224/224 | 158/158 | 222/226 | 154/154 | 157/157 | 160/162 | 137/153 | 158/164 | 154/156 | 157/183 |
| SD47 | 229/229 | 202/224 | 158/158 | 222/226 | 142/154 | 157/157 | 158/158 | 153/153 | 158/158 | 154/154 | 157/157 |
| SD37 | 229/229 | 202/224 | 158/158 | 226/226 | 142/154 | 157/163 | 158/162 | 137/159 | 156/164 | 154/156 | 153/157 |
| HN5 | 229/231 | 224/224 | 158/158 | 222/226 | 142/154 | 157/157 | 158/160 | 153/159 | 166/166 | 154/156 | 157/157 |
| HN06 | 227/229 | 202/202 | 150/158 | 226/226 | 142/154 | 157/157 | 154/158 | 137/137 | 156/164 | 154/154 | 157/157 |
| HN4 | 217/217 | 202/224 | 150/158 | 222/226 | 142/154 | 157/157 | 154/158 | 153/161 | 164/164 | 154/154 | 189/189 |
| SXXA18 | 231/231 | 224/224 | 158/158 | 222/222 | 142/142 | 157/157 | 160/160 | 159/161 | 166/166 | 154/156 | 161/183 |
| SXXA1 | 215/229 | 222/224 | 158/158 | 226/226 | 142/142 | 157/157 | 154/154 | 137/161 | 164/164 | 154/154 | 183/183 |
| CY01 | 229/229 | 224/224 | 158/158 | 224/224 | 142/142 | 157/157 | 154/154 | 137/159 | 160/160 | 148/148 | 140/140 |
| XJ02 | 233/233 | 202/202 | 150/150 | 226/226 | 142/154 | 157/157 | 154/154 | 137/159 | 164/164 | 154/154 | 157/157 |
| WG02 | 227/229 | 224/224 | 148/156 | 226/226 | 142/154 | 157/157 | 158/158 | 137/159 | 162/164 | 156/156 | 153/153 |
| MK02 | 213/213 | 202/224 | 158/158 | 224/224 | 142/142 | 157/157 | 154/154 | 159/159 | 158/158 | 154/154 | 153/153 |
| HY24 | 229/229 | 202/202 | 158/158 | 222/222 | 154/154 | 157/157 | 158/162 | 153/153 | 158/170 | 154/154 | 157/157 |

Variety identification is determined by the number of differential loci, two varieties having differential loci ≥3 are considered as different varieties, those having differential loci <3 are considered as substantially similar or the same varieties. Comparing to the fingerprint data of 23 pomegranate materials, it is found that the number of differential loci between any two of the materials is greater than 3, indicating that the 11 core primer pairs may effectively identify these pomegranate resources. NTSYS-pc V2.10e software is used to calculate the coefficients of genetic similarity among varieties, an UPGMA method is used to conduct a cluster analysis to generate a phylogenetic tree as shown in FIG. 1.

cepts. Moreover, while the concepts have been disclosed with specific reference to certain implementations, a person of ordinary skill in the art may recognize that changes may be made in form and detail without departing from the scope of those concepts. As such, the disclosed implementations are to be considered in all respects as illustrative and not restrictive. It should also be understood that the present disclosure is not limited to the particular implementations disclosed and many rearrangements, modifications, and substitutions are possible without departing from the scope of the present disclosure.

What is claimed is:

1. A method for identifying a variety of a plant of a genus pomegranate, the method comprising:

extracting DNA from the plant;

conducting a polymerase chain reaction (PCR) using the extracted DNA and a Simple Sequence Repeat (SSR) primer group comprising 11 primer pairs, the 11 primer pairs comprise PG080, PG130, PG139, PG152, PG153, PG140, PG098, PG070, PG077, PG090, and PG093, wherein nucleotide sequences of each of the 11 primer pairs are as follows:

| Sequence ID | Primer | Forward primer |
|---|---|---|
| 1 | PG080 | ctgactgttgcagagagtaggctg |
| 3 | PG130 | ctcatatggcgattctctgtcctt |
| 5 | PG139 | gtttccttccctcaacccaaaa |
| 7 | PG152 | catcagaatcgtcccttgtg |
| 9 | PG153 | gtgtttgatgctcccatttcattt |

| Sequence ID | Primer | Forward primer |
|---|---|---|
| 11 | PG140 | caagaaagtgtgtgagcgattgat |
| 13 | PG098 | tgccttcttaaggacttcaccaac |
| 15 | PG070 | cacctctgcttcagcaaacaaata |
| 17 | PG077 | gtcagtctcctccttcttcaatgg |
| 19 | PG090 | attcttttatactaaccaaaatttgcga |
| 21 | PG093 | cgtcaataggacgtccctgagata |

| Sequence ID | Primer | Reverse primer |
|---|---|---|
| 2 | PG080 | aggaggtgaaacaacgaatagctg |
| 4 | PG130 | aagttcgataaattgcactggtgg |
| 6 | PG139 | agtgggattttaccaagtcgaaca |
| 8 | PG152 | cagagagaagaagagagaccgagc |
| 10 | PG153 | gccttcaacggtctttcttcttct |
| 12 | PG140 | ccaaaccttacccctctctctctc |
| 14 | PG098 | ctaacctcatgcacttgtcatcca |
| 16 | PG070 | caactcaacacaatatccaaccca |
| 18 | PG077 | agacgaagcacctgagaaggaat |
| 20 | PG090 | atgtcatgagaggacccacaaa |
| 22 | PG093 | gatgacgtggcagagtaagagagc; | obtaining amplified DNA products;

analyzing SSR polymorphisms of the amplified DNA products; and identifying the variety of the plant based on the polymorphic amplified DNA products.

2. The method of claim 1, further comprising:

constructing a DNA fingerprint for the variety of the plant based on the analysis of SSR polymorphisms.

3. A method for distinguishing pomegranate plant varieties, the method comprising:

extracting DNAs from at least two plants of the pomegranate genus;

conducting a polymerase chain reaction (PCR) using the extracted DNAs and a Simple Sequence Repeat (SSR) primer group comprising 11 primer pairs, the 11 primer pairs comprise PG080, PG130, PG139, PG152, PG153, PG140, PG098, PG070, PG077, PG090, and PG093, wherein nucleotide sequences of each of the 11 primer pairs are as follows:

| Sequence ID | Primer | Forward primer |
|---|---|---|
| 1 | PG080 | ctgactgttgcagagagtaggctg |
| 3 | PG130 | ctcatatggcgattctctgtcctt |
| 5 | PG139 | gtttccttccctcaacccaaaa |
| 7 | PG152 | catcagaatcgtcccttgtg |
| 9 | PG153 | gtgtttgatgctcccatttcattt |
| 11 | PG140 | caagaaagtgtgtgagcgattgat |
| 13 | PG098 | tgccttcttaaggacttcaccaac |
| 15 | PG070 | cacctctgcttcagcaaacaaata |
| 17 | PG077 | gtcagtctcctccttcttcaatgg |
| 19 | PG090 | attcttttatactaaccaaaatttgcga |
| 21 | PG093 | cgtcaataggacgtccctgagata |

| Sequence ID | Primer | Reverse primer |
|---|---|---|
| 2 | PG080 | aggaggtgaaacaacgaatagctg |
| 4 | PG130 | aagttcgataaattgcactggtgg |
| 6 | PG139 | agtgggattttaccaagtcgaaca |
| 8 | PG152 | cagagagaagaagagagaccgagc |
| 10 | PG153 | gccttcaacggtctttcttcttct |
| 12 | PG140 | ccaaaccttacccctctctctctc |
| 14 | PG098 | ctaacctcatgcacttgtcatcca |
| 16 | PG070 | caactcaacacaatatccaaccca |
| 18 | PG077 | agacgaagcacctgagaaggaat |
| 20 | PG090 | atgtcatgagaggacccacaaa |
| 22 | PG093 | gatgacgtggcagagtaagagagc; | obtaining amplified DNA products for each plant;

determining allele sizes of the amplified DNA products corresponding to each of the 11 primer pairs; and comparing the allele sizes across the at least two plants, such that if the allele sizes of the DNA products corresponding to each of the 11 primer pairs are determined to be different in 3 or more of the allele sizes of the 11 primer pairs, the two plants are detellinned to be different varieties.

* * * * *

SEQUENCE LISTING

```
Sequence total quantity: 22
SEQ ID NO: 1            moltype = DNA   length = 24
FEATURE                 Location/Qualifiers
misc_feature            1..24
                        note = PG080 FORWARD PRIMER
source                  1..24
                        mol_type = other DNA
                        organism = synthetic construct
SEQUENCE: 1
ctgactgttg cagagagtag gctg                                             24

SEQ ID NO: 2            moltype = DNA   length = 24
FEATURE                 Location/Qualifiers
misc_feature            1..24
                        note = PG080 Reverse Primer
source                  1..24
                        mol_type = other DNA
                        organism = synthetic construct
SEQUENCE: 2
aggaggtgaa acaacgaata gctg                                             24

SEQ ID NO: 3            moltype = DNA   length = 24
FEATURE                 Location/Qualifiers
misc_feature            1..24
                        note = PG130 Forward Primer
source                  1..24
                        mol_type = other DNA
                        organism = synthetic construct
SEQUENCE: 3
ctcatatggc gattctctgt cctt                                             24

SEQ ID NO: 4            moltype = DNA   length = 24
FEATURE                 Location/Qualifiers
misc_feature            1..24
                        note = PG130 Reverse Primer
source                  1..24
                        mol_type = other DNA
                        organism = synthetic construct
SEQUENCE: 4
aagttcgata aattgcactg gtgg                                             24

SEQ ID NO: 5            moltype = DNA   length = 22
FEATURE                 Location/Qualifiers
misc_feature            1..22
                        note = PG139 Forward Primer
source                  1..22
                        mol_type = other DNA
                        organism = synthetic construct
SEQUENCE: 5
gtttccttcc ctcaacccaa aa                                               22

SEQ ID NO: 6            moltype = DNA   length = 24
FEATURE                 Location/Qualifiers
misc_feature            1..24
                        note = PG139 Reverse Primer
source                  1..24
                        mol_type = other DNA
                        organism = synthetic construct
SEQUENCE: 6
agtgggattt taccaagtcg aaca                                             24

SEQ ID NO: 7            moltype = DNA   length = 21
FEATURE                 Location/Qualifiers
misc_feature            1..21
                        note = PG152 Forward Primer
source                  1..21
                        mol_type = other DNA
                        organism = synthetic construct
SEQUENCE: 7
catcagaatc gtccccttgt g                                                21

SEQ ID NO: 8            moltype = DNA   length = 24
FEATURE                 Location/Qualifiers
misc_feature            1..24
                        note = PG152 Reverse Primer
source                  1..24
                        mol_type = other DNA
                        organism = synthetic construct
```

```
SEQUENCE: 8
cagagagaag aagagagacc gagc                                                  24

SEQ ID NO: 9            moltype = DNA   length = 24
FEATURE                 Location/Qualifiers
misc_feature            1..24
                        note = PG153 Forward Primer
source                  1..24
                        mol_type = other DNA
                        organism = synthetic construct
SEQUENCE: 9
gtgtttgatg ctcccatttc attt                                                  24

SEQ ID NO: 10           moltype = DNA   length = 24
FEATURE                 Location/Qualifiers
misc_feature            1..24
                        note = PG153 Reverse Primer
source                  1..24
                        mol_type = other DNA
                        organism = synthetic construct
SEQUENCE: 10
gccttcaacg gtctttcttc ttct                                                  24

SEQ ID NO: 11           moltype = DNA   length = 24
FEATURE                 Location/Qualifiers
misc_feature            1..24
                        note = PG140 Forward Primer
source                  1..24
                        mol_type = other DNA
                        organism = synthetic construct
SEQUENCE: 11
caagaaagtg tgtgagcgat tgat                                                  24

SEQ ID NO: 12           moltype = DNA   length = 24
FEATURE                 Location/Qualifiers
misc_feature            1..24
                        note = PG140 Reverse Primer
source                  1..24
                        mol_type = other DNA
                        organism = synthetic construct
SEQUENCE: 12
ccaaacctta cccctctctc tctc                                                  24

SEQ ID NO: 13           moltype = DNA   length = 24
FEATURE                 Location/Qualifiers
misc_feature            1..24
                        note = PG098 Forward Primer
source                  1..24
                        mol_type = other DNA
                        organism = synthetic construct
SEQUENCE: 13
tgccttctta aggacttcac caac                                                  24

SEQ ID NO: 14           moltype = DNA   length = 24
FEATURE                 Location/Qualifiers
misc_feature            1..24
                        note = PG098 Reverse Primer
source                  1..24
                        mol_type = other DNA
                        organism = synthetic construct
SEQUENCE: 14
ctaacctcat gcacttgtca tcca                                                  24

SEQ ID NO: 15           moltype = DNA   length = 24
FEATURE                 Location/Qualifiers
misc_feature            1..24
                        note = PG070 Forward Primer
source                  1..24
                        mol_type = other DNA
                        organism = synthetic construct
SEQUENCE: 15
cacctctgct tcagcaaaca aata                                                  24

SEQ ID NO: 16           moltype = DNA   length = 24
FEATURE                 Location/Qualifiers
misc_feature            1..24
                        note = PG070 Reverse Primer
source                  1..24
                        mol_type = other DNA
```

```
                        organism = synthetic construct
SEQUENCE: 16
caactcaaca caatatccaa ccca                                              24

SEQ ID NO: 17           moltype = DNA   length = 24
FEATURE                 Location/Qualifiers
misc_feature            1..24
                        note = PG077 Forward Primer
source                  1..24
                        mol_type = other DNA
                        organism = synthetic construct
SEQUENCE: 17
gtcagtctcc tccttcttca atgg                                              24

SEQ ID NO: 18           moltype = DNA   length = 23
FEATURE                 Location/Qualifiers
misc_feature            1..23
                        note = PG077 Reverse Primer
source                  1..23
                        mol_type = other DNA
                        organism = synthetic construct
SEQUENCE: 18
agacgaagca cctgagaagg aat                                               23

SEQ ID NO: 19           moltype = DNA   length = 28
FEATURE                 Location/Qualifiers
misc_feature            1..28
                        note = PG090 Forward Primer
source                  1..28
                        mol_type = other DNA
                        organism = synthetic construct
SEQUENCE: 19
attcttttat actaaccaaa atttgcga                                          28

SEQ ID NO: 20           moltype = DNA   length = 22
FEATURE                 Location/Qualifiers
misc_feature            1..22
                        note = PG090 Reverse Primer
source                  1..22
                        mol_type = other DNA
                        organism = synthetic construct
SEQUENCE: 20
atgtcatgag aggacccaca aa                                                22

SEQ ID NO: 21           moltype = DNA   length = 24
FEATURE                 Location/Qualifiers
misc_feature            1..24
                        note = PG093 Forward Primer
source                  1..24
                        mol_type = other DNA
                        organism = synthetic construct
SEQUENCE: 21
cgtcaatagg acgtccctga gata                                              24

SEQ ID NO: 22           moltype = DNA   length = 24
FEATURE                 Location/Qualifiers
misc_feature            1..24
                        note = PG093 Reverse Primer
source                  1..24
                        mol_type = other DNA
                        organism = synthetic construct
SEQUENCE: 22
gatgacgtgg cagagtaaga gagc                                              24
```